United States Patent [19]

Saeki et al.

[11] Patent Number: 5,035,899
[45] Date of Patent: Jul. 30, 1991

[54] PERORAL PREPARATION OF ACID-UNSTABLE COMPOUND

[75] Inventors: Yasuharu Saeki, Tsukuba; Noritoshi Koyama, Ibaraki; Sumio Watanabe, Aichi; Shigeru Aoki, Gifu, all of Japan

[73] Assignee: Eisai Co., Ltd., Tokyo, Japan

[21] Appl. No.: 332,731

[22] Filed: Apr. 4, 1989

[30] Foreign Application Priority Data

May 18, 1988 [JP] Japan ................................. 63-121233

[51] Int. Cl.$^5$ .............................................. A61K 9/36
[52] U.S. Cl. .................................. 424/480; 424/465; 424/482; 427/3
[58] Field of Search ....................... 424/465, 480, 482; 427/3

[56] References Cited

U.S. PATENT DOCUMENTS 4,786,505 11/1988 Lovgren et al. ..................... 424/468
4,853,230 8/1989 Lovgren et al. ................. 424/468 X

FOREIGN PATENT DOCUMENTS 0268956 6/1988 European Pat. Off. .

Primary Examiner—Thurman Page
Assistant Examiner—D. Gabrielle Phelan
Attorney, Agent, or Firm—Nixon & Vanderhye

[57] ABSTRACT

A peroral preparation of an acid-unstable compound comprises (1) a core containing the acid-unstable compound, (2) a first layer, coated on the core, comprising a hardly water-soluble, film-forming material and fine particles of a hardly water-soluble substance, suspended in the material, and (3) a second layer, coated on the first layer, of enteric film. The acid-unstable compound is a benzimidazole compound.

6 Claims, No Drawings

PERORAL PREPARATION OF ACID-UNSTABLE COMPOUND

This invention relates to a novel stabilized peroral preparation containing an acid-unstable compound.

Prior Art

Benzimidazole derivatives having an $H^+$-$K^+$ATPase inhibition effect, which are now on the way of development, are useful in the treatment of digestive ulcers, since they would intensely suppress the secretion of gastric acid. Since these compounds exert intense and persistent effects, they attract public attention as novel drugs for treating digestive ulcers which substitute for histamin $H_2$ receptor antagonists such as cimetidine. Animal tests have indicated that 2-[{4-(3-methoxypropoxy)3-methylpyridin-2-yl}methylsulfinyl]-1H-benzimidazole sodium, among these compounds, has a particularly intense effect of suppressing gastric acid secretion and an appropriate duration of the action. Thus it is expected to be clinically useful.

However the abovementioned benzimidazole derivatives are poor in stability. In particular, they would be rapidly decomposed and colored under moist conditions or in an acidic to neutral aqueous solution. When these compounds are to be formulated into a preparation for oral administration, therefore, it should be coated with an enteric coating to thereby prevent the decomposition of the same with gastric acid. However an enteric coating is an acidic material which is insoluble in water under acidic conditions and soluble in water under neutral to alkaline conditions. Thus the coating of a core comprising an acid-unstable compound, e.g., a benzimidazole derivative with such an enteric coating might generally cause the decomposition of said acid-unstable compound. Such decomposition occurs even during the enteric coating stage by a common method, for example, with the use of a fluidized bed coater, which results in the coloration of the surface of the core. Further the storage stability of the coated core as well as the stability in an acidic solution of the same might be lowered thereby.

In order to avoid these difficulties, Japanese Patent Laid-Open No. 258316/1987 and No. 258320/1987 disclose each a method comprising intermediately coating the core containing an acid-unstable compound with a material soluble in water or decomposable in water and then further coating the same with an enteric coating. However these methods cannot sufficiently stabilize an acid-unstable compound and therefore further improvement is required.

SUMMARY OF THE INVENTION

The present inventors have conducted extensive studies in order to further stabilize an acid-unstable compound contained in a core. As a result, they have found that the conventional methods can be improved by intermediately coating said core with both fine particles of a hardly water-soluble material and a hardly water-soluble film-forming material, thus completing the present invention.

Accordingly, the present invention provides a peroral preparation of an acid-unstable compound characterized in that a core containing an acid-unstable compound is coated with a hardly water-soluble film-forming material containing a suspended, hardly water-soluble fine material, and further coated with an enteric coating.

A peroral preparation of an acid-unstable compound, according to the invention, comprises (1) a core containing the acid-unstable compound, (2) a first layer, coated on the core, comprising a hardly water-soluble, film-forming material and fine particles of a hardly water-soluble substance, suspended in the material, and (3) a second layer, coated on the first layer, of enteric film. The acid-unstable compound is preferred to be a benzimidazole compound.

The benzimidazole compound to use in the invention is disclosed in EP-A 268 956.

The core may contain a pharmacologically effective amount of a pharmacologically effective, acid-unstable compound. A most preferable, acid-unstable compound is sodium salt of 2((4-(3-methoxypropoxy)-3-methylpyridin-2-yl)methylsulfinyl)-1H-benzimidazol.

It is preferable that a weight ratio to the substance to the material is not less than 5 percent.

Now the present invention will be described in detail. The term "core" used herein refers to those conventionally used for oral administration, such as tablets, granules, fine subtilaes and capsules. The core may be prepared in a conventional manner. For example, a core in tablet form may be obtained by mixing an acid-unstable compound with excipients such as mannitol or lactose and binders such as hydroxypropylcellulose or polyvinylpyrrolidone, granulating the obtained mixture by fluidized bed granulation or tumbling granulation and then tableting the granules. As the acid-unstable compound, a benzimidazole derivatives, in particular, 2-[{4-(3-methoxypropoxy)-3-methylpyridin-2-yl}methylsulfinyl]1H-benzimidazole sodium, which will be simply referred to as the material S hereinafter, may be preferably employed.

Examples of the hardly water-soluble fine material to be used as the intermediate coating layer in the present invention include magnesium oxide, silicic anhydride, calcium silicate, magnesium hydroxide, magnesium carbonate, aluminum hydroxide, calcium stearate, magnesium stearate and sucrose fatty acid esters. Either one of these materials or a mixture thereof may be used in the present invention. Examples of the hardly water-soluble film-forming material include ethylcellulose and polyvinyl acetate. It is preferable to use at least 5% by weight, still preferably at least 10% by weight, of the hardly water-soluble fine material based on the hardly water-soluble film-forming material. When the ratio of the fine material to the film-forming material is lower than 5% by weight, the disintegration of the core takes a prolonged period of time and thus the liberation of the active ingredient is retarded. The ratio of the fine material to the film-forming material may be increased up to such a level as not to inhibit the coating procedure.

In the present invention, the formation of the intermediate coating layer by coating the core with both said hardly water-soluble fine material and said hardly water-soluble film-forming material may be conducted in the following manner. Namely, the film-forming material is dissolved in a solvent such as ethanol and then the fine material is thoroughly suspended therein with the use of, for example, Polytron. ® The obtained suspension may be sprayed onto the core in a conventional manner, for example, with the use of a fluidized bed coater to thereby form the aimed intermediate coating layer.

Then the core thus coated with the intermediate coating layer is further coated with an enteric coating to thereby give a stabilized peroral preparation of an acid-unstable compound according to the present invention. The coating with an enteric coating may be carried out in a conventional manner. Namely, the enteric material is dissolved or suspended in a solvent optionally together with a plasticizer, and the solution thus obtained is applied onto the intermediately coated core in a conventional manner with, for example, a fluidized bed coater.

Examples of the enteric material to be used in the present invention include hydroxypropylmethylcellulose phthalate, cellulose acetate phthalate, methacrylic acid/methyl methacrylate copolymer and polyvinyl acetate phthalate.

EXAMPLES

To further illustrate the present invention, and not by way of limitation, the following Examples will be given, wherein all parts and percentages are by weight, unless otherwise noted.

EXAMPLE 1

The material S, mannitol and magnesium oxide were mixed together. To the obtained mixture was added hydroxypropylcellulose dissolved in ethanol. The mixture was granulated, dried and passed through a 28-mesh sieve to give granules (A). Separately crystalline cellulose was mixed with corn starch and hydroxypropylcellulose dissolved in water was added thereto. The obtained mixture was granulated, dried and passed through a 28-mesh sieve to give granules (B). The granules (A) and (B), carboxymethylcellulose, talc and magnesium stearate were mixed together and treated with a single-shot tablet machine (mfd. by Okada Seiko K. K.). Thus uncoated tablets of the following composition each weighing 120.2 mg were obtained.

| Composition: | parts |
|---|---|
| material S | 5 |
| mannitol | 45.3 |
| magnesium oxide | 40 |
| hydroxypropylcellulose | 2.5 |
| crystalline cellulose | 10 |
| corn starch | 10 |
| carboxymethylcellulose calcium | 5 |
| talc | 2 |
| magnesium stearate | 0.2. |

60 g of ethylcellulose was dissolved in 540 g of ethanol and 40 g of silicic anhydride was dispersed in the obtained solution. The uncoated tablets obtained above were intermediately coated with the dispersion thus obtained by using a fluidized bed coater (GLATT WSG-3). Thus intermediately coated tablets each weighing 122.8 mg were obtained.

Next, 300 g of hydroxypropylmethylcellulose phthalate, 15 g of titanium oxide, 30 g of talc and 30 g of a glycerol fatty acid ester ( Myvacet ® 9-40T) were dissolved and/or dispersed in a mixture of 80% ethanol with water. The above-described tablets were coated with the solution thus obtained in a fluidized bed coater. Thus enteric tablets each weighing 131.7 mg were obtained.

EXAMPLE 2

50 g of ethylcellulose was dissolved in 500 g of ethanol and 50 g of magnesium oxide was dispersed in the obtained solution. The uncoated tablets obtained in Example 1 were intermediately coated with the above dispersion. Thus intermediately coated tablets each weighing 122.6 mg were obtained. Next, 300 g of hydroxypropylmethylcellulose phthalate, 15 g of titanium oxide, 30 g of talc and 30 g of a glycerol fatty acid ester ( Myvacet ® 9-40T) were dissolved and/or dispersed in a mixture of 80% ethanol with water. The intermediately coated tablets described above were then coated with the resulting solution in a fluidized bed coater. Thus enteric tablets each weighing 132.0 mg were obtained.

EXAMPLE 3

The material S was mixed with mannitol. To the obtained mixture was added hydroxypropylcellulose dissolved in ethanol. The resulting mixture was granulated, dried and passed through a 28-mesh sieve to give granules (A), which were mixed with crystalline cellulose, corn starch, carboxymethylcellulose potassium, talc and magnesium stearate. The mixture was treated with a single-shot tablet machine to thereby give uncoated tablets of the following composition each weighing 99.7 mg.

| Composition: | part |
|---|---|
| material S | 5 |
| mannitol | 65.3 |
| hydroxypropylcellulose | 2.5 |
| crystalline cellulose | 10 |
| corn starch | 10 |
| carboxymethylcellulose calcium | 5 |
| talc | 2 |
| magnesium stearate | 0.2. |

60 g of ethylcellulose was dissolved in 540 g of ethanol and 6 g of silicic anhydride was dispersed in the obtained solution. The uncoated tablets obtained above were intermediately coated with this dispersion in a fluidized bed coater. Thus intermediately coated tablets each weighing 102.5 mg were obtained. Next, 300 g of hydroxypropylmethylcellulose phthalate, 15 g of titanium oxide, 30 g of talc and 30 g of a glycerol fatty acid ester ( Myvacet ® 9-40T) were dissolved and/or dispersed in a mixture of 80% ethanol with water. The intermediately coated tablets obtained above were further coated with the resulting solution in a fluidized bed coater. Thus enteric tablets each weighing 112.2 mg were obtained.

REFERENTIAL EXAMPLE 30 g of hydroxypropylcellulose was dissolved in 600 g of ethanol. The uncoated tablets obtained in Example 1 were intermediately coated with the resulting solution in a fludizied bed coater. Thus intermediately coated tablets each weighing 122.8 mg were obtained. Next, 300 g of hydroxypropylmethylcellulose, 15 g of titanium oxide, 30 g of talc and 30 g of a glycerol fatty acid ester ( Myvacet ® 9-40T) were dissolved and/or dispersed in a mixture of 80% ethanol with water. The abovementioned intermediately coated tablets were further coated with the solution thus obtained. Thus enteric tablets each weighing 131.4 mg were obtained.

EXAMPLE 4

60 g of ethylcellulose was dissolved in 740 g of ethanol and 80 g of special calcium silicate was dispersed in the obtained solution. The uncoated tablets obtained in Example 3 were intermediately coated with the resulting dispersion. Thus intermediately coated tablets each weighing 101.9 mg were obtained. Next, 300 g of hydroxypropylmethylcellulose phthalate, 15 g of titanium oxide, 30 g of talc and 30 g of a glycerol fatty acid ester (Myvacet ® 9-40T) were dissolved and/or dispersed in a mixture of 80% ethanol with water. The above intermediately coated tablets were further coated with the resulting solution. Thus enteric tablets each weighing 112.0 mg were obtained.

EXAMPLE 5

60 g of ethylcellulose was dissolved in 540 g of ethanol and 30 g of calcium stearate and 30 g of sucrose di- and tri-stearate were dispersed in the obtained solution. The uncoated tablets obtained in Example 3 were intermediately coated with the resulting dispersion. Thus intermediately coated tablets each weighing 100.8 mg were obtained. Next, 300 g of hydroxypropylmethylcellulose phthalate, 15 g of titanium oxide, 30 g of talc and 30 g of a glycerol fatty acid ester (Myvacet ® 9-40T) were dissolved and/or dispersed in a mixture of 80% ethanol with water. The above intermediately coated tablets were further coated with the resulting solution. Thus enteric tablets each weighing 109.5 mg were obtained.

EXAMPLE 6

60 g of ethylcellulose was dissolved in 540 g of ethanol and 30 g of magnesium carbonate was dispersed in the obtained solution. The uncoated tablets obtained in Example 3 were intermediately coated with the resulting dispersion. Thus intermediately coated tablets each weighing 102.0 mg were obtained. Next, 300 g of methacrylic acid/methyl methacrylate copolymer, 15 g of titanium oxide, 30 g of talc and 30 g of triacetylglcyerol were dissolved and/or dispersed in a mixture of ethanol with methylene chloride. The above intermediately coated tablets were further coated with the resulting solution. Thus enteric tablets each weighing 112.5 mg were obtained.

EXAMPLE 7

60 g of polyvinyl acetate was dissolved in a mixture of ethanol with methylene chloride (1 : 1) and 60 g of magnesium oxide was dispersed in the obtained solution. The uncoated tablets obtained in Example 3 were intermediately coated with the resulting dispersion. Thus intermediately coated tablets each weighing 101.0 mg were obtained. Next, 300 g of hydroxypropylmethylcellulose phthalate, 15 g of titanium oxide, 30 g of talc and 30 g of a glycerol fatty acid ester (Myvacet ® 9-40T) were dissolved and/or dispersed in a mixture of 80% ethanol with water. The above intermediately coated tablets were further coated with the resulting solution. Thus enteric tablets each weighing 110.4 mg were obtained.

Effects of the Invention

To further illustrate the effects of the present invention, the following Test Examples will be given.

TEST EXAMPLE 1

The enteric tablets obtained in the above Examples 1 and 2 and Referential Example were shaken in the 1st fluid as specified in the Pharmacopoeia of Japan and the appearance of each tablet was observed. Table 1 shows the results.

TABLE 1

| Sample/Time (hr) | 2 | 4 | 6 | 8 |
|---|---|---|---|---|
| Ex. 1 | − | − | − | − |
| Ex. 2 | − | − | − | − |
| Ref. Ex. | − | ± | ± | + |

Note:
−: Not changed (white).
±: Somewhat changed (slightly yellow).
+: Changed (yellowish brown).

Table 1 obviously indicates that the appearance of the tablet of Referential Example 1 changed after shaking for four hours, while those of Examples 1 and 2 showed no change after shaking for eight hours.

TEST EXAMPLE 2

The enteric tablets obtained in the above Examples 1 and 2 and Referential Example were stored either at 25° C. and at a relative humidity of 75% or at 40° C. and at a relative humidity of 75% for one week and the appearance of each tablet was observed. Table 2 shows the results.

TABLE 2

| Sample/Temp./RH conditions | 25° C., RH 75% | 40° C., RH 75% |
|---|---|---|
| Ex. 1 | − | ± |
| Ex. 2 | − | ± |
| Ref. Ex. | ± | + |

Note:
−: Not changed (white).
±: Somewhat changed (slightly yellow).
+: Changed (blueish black).

Table 2 obviously indicates that the tablet obtained in Referential Example showed a change at 25° C. and at a relative humidity of 75% and significantly colored at 40° C. and at a relative humidity of 75%. On the other hand, those of the Examples 1 and 2 showed no change at 25° C. and at a relative humidity of 75% and slightly colored at 40° C. and at a relative humidity of 75%.

TEST EXAMPLE 3

The disintegration periods of the tablets obtained in the above Examples 1 and 2 and Referential Example were determined according to the Disintegration Test (with 2nd fluid) specified in the Pharmacopoeia of Japan. Table 3 shows the results.

TABLE 3

| Sample | Disintegration period (hr) |
|---|---|
| Ex. 1 | 7.4–7.8 |
| Ex. 2 | 7.7–8.0 |
| Ref. Ex. | 7.2–7.8 |

Table 3 obviously indicates that the enteric tablets of Examples 1 and 2 are comparable to that of Referential Example in the disintegration period without showing any prolongation thereof.

We claim:
1. A peroral preparation of a benzimidazole compound, which consists essentially of:
 (1) a core containing a pharmacologically effective amount of a pharmacologically effective, acid-unstable benzimidazole compound,
 (2) a slightly water-soluble first coating layer, coated on the core, comprising a slightly water-soluble, film-forming material selected from the group consisting of ethyl cellulose and polyvinyl acetate and fine particles of a slightly water-soluble substance selected from the group consisting of magnesium oxide, silicic anhydride, calcium silicate, magnesium hydroxide, magnesium carbonate, aluminum hydroxide, calcium stearate, magnesium stearate and sucrose fatty acid esters suspended in the first layer, and (3) a second coating layer, coated on the first layer, of an enteric polymer film.

2. A peroral preparation as claimed in claim 1 or 2, in which the acid-unstable compound is a benzimidazole compound.

3. A peroral preparation as claimed in claim 1, in which the acid-unstable compound is sodium salt of 2(4-(3-methoxypropoxy)-3-methylpyridin-2-yl)methylsulfinyl)-1H-benzimidazol.

4. A peroral preparation as claimed in claim 1 or 3, in which a weight ratio to the substance to the material is not less than 5 percent.

5. A peroral preparation as claimed in claim 1 or 3, in which the enteric film is selected from the group consisting of hydroxypropylmethylcellulose phthalate, cellulose acetate phthalate, a copolymer of methacrylic acid and methyl methacrylate, and polyvinyl acetate phthalate.

6. A peroral preparation as claimed in claim 1 or 3, in which the second coating layer also contains a plasticizer.

* * * * *